United States Patent [19]

Müeller

[11] Patent Number: 4,971,447
[45] Date of Patent: Nov. 20, 1990

[54] METHOD FOR MEASURING CONCENTRATION OF CHEMICAL SUBSTANCES

[75] Inventor: Rüdolf Müeller, Soecking, Fed. Rep. of Germany

[73] Assignee: Siemens Aktiengesellschaft, Berlin and Munich, Fed. Rep. of Germany

[21] Appl. No.: 314,083

[22] Filed: Feb. 23, 1989

[30] Foreign Application Priority Data

Mar. 17, 1988 [DE] Fed. Rep. of Germany ....... 3809013

[51] Int. Cl.$^5$ ............................................. G01J 3/51
[52] U.S. Cl. .................................... 356/419; 250/226
[58] Field of Search ....................... 356/328, 419, 412; 250/226

[56] References Cited

U.S. PATENT DOCUMENTS

| | | | |
|---|---|---|---|
| 3,717,412 | 2/1973 | Takuma et al. | 356/303 X |
| 4,054,389 | 10/1977 | Owen | 356/419 |
| 4,200,110 | 4/1980 | Peterson et al. | 356/412 X |
| 4,267,572 | 5/1981 | Witte | 364/489 |
| 4,278,538 | 7/1981 | Lawrence et al. | 250/226 X |
| 4,484,817 | 11/1984 | Nobuto | 356/416 |
| 4,520,381 | 5/1985 | Moriguchi et al. | 250/226 X |
| 4,560,275 | 12/1985 | Goetz | 356/328 X |
| 4,677,289 | 6/1987 | Nozaki et al. | 250/226 |
| 4,766,551 | 8/1988 | Begley | 356/328 X |

OTHER PUBLICATIONS

Japanese Abstract, vol. 6, No. 217P1521095 of Oct. 30, 1982.
Japanese Patent Abstract, vol. 9, No. 37P3351760, Feb. 16, 1985, No. 59-180310.
Article by W. Albertshofer, A. Gerhard Lehrstuhl fur Technische Elektronic, TU Muenchen Lehrstuhl fur Nachrichtentechnik TU Muenchen.

*Primary Examiner*—Vincent P. McGraw
*Attorney, Agent, or Firm*—Hill, Van Santen, Steadman & Simpson

[57] ABSTRACT

A method for optical identification of the concentration of at least one substance which can be observed in a medium (12) directly due to its own color or indirectly with the use of a color indicator. Chromatic light is measured using a number of independent photodiodes which are sensitive in different absorption regions and the measured values thus obtained are compiled in a pattern matrix and are evaluated using pattern recognition, and the concentration of the substance is identified using known comparison values. An electrical structure (14) formed with a number of different photodiodes integrated therein is used. The method is suitable for exact and reproducible measurements of concentrations which can be identified by their color and it can be implemented in a simple manner.

4 Claims, 2 Drawing Sheets

METHOD FOR MEASURING CONCENTRATION OF CHEMICAL SUBSTANCES

BACKGROUND OF THE INVENTION

1. Field of the Invention

This invention relates in general to methods for optically identifying concentration of substances that can be directly observed in a medium using the inherent color of the substance or by indirectly observing the substance with the use of a color indicator.

2. Description of Related Art

There are many different physical chemical methods which can be utilized for identifying concentration of a substance for example, in a light medium. In most instances, however, involved methods are complicated and large and stationary apparatus are needed for this purpose. Thus, exact concentration measurements are usually only possible in a laboratory and are carried out there using spectrometers, gas chromatographs, elementary analyzers and other expensive and complicated apparatus.

When there is a problem of measuring concentration quickly outside of the laboratory as, for example, outdoors, than optical methods can be utilized for a number of such measurements. For example, the use of the colorations of the substance to be measured which are dependent on the specific concentrations of the substance or the use of a color indicator that responds to this substance can be used. An example of such an indication is that of pH value measurement using color indicators. The color indicators are substances which change color or loose their color at different pH values.

Since only two pH regions can be distinguished using a single indicator, suitable mixtures of indicators are currently used which yield a hue which varies over a greater pH value range. For identifying the exact value, this hue is compared to a color scale and the pH value is then read from the color scale.

This evaluation method using color comparison however, is extremely subjective and is significantly more difficult if not impossible if further color substances or a contaminate, for example, waste water, are present in the sample solution.

See also U.S. Pat. Nos. 4,560,275, 4,484,817, 4,677,289, 4,267,572, Patent Abstracts of Japan, Vol. 6, No. 217 (P-152) 1095 Oct.30, 1982 No. 57-120829,Matsushita Denki Sangyo, Patent Abstracts of Japan, Vol. 9,No. 37 (P-335) (1760) Feb. 16, 1985, No. 59-180310-,Fijitsu KK, the article by W. Albertshofer, A. Gerhard, Flussigkeitsanalyse unter Verwendung einer Spektrometer diode, Proceedings of Sensoren-Technologie und Anwendung, Bad Nauheim, FRG, 1986, NTG-Fachberichte 93, appendix, page 30,German Application No. DE P 37 36 201.1, German application No. DEP3743 131.5 which corresponds to U.S. application Ser. No. 261,489 and German application P 37 36 203.8.

SUMMARY OF THE INVENTION

It is an object of the present invention to provide a method for measuring concentration of a colorant or for identifying the hue of an indicator or an indicator system which is simple to operate and allows an objective evaluation and which is accurate and allows rapid concentration measurements.

In the invention, light emitted by the medium that indicates the color is measured in different absorption regions of sensitive independent photodiodes and the measurement values are then combined in a pattern matrix and are evaluated using pattern recognition and the concentration of the substance or substances is identified by referring to known comparison values.

The observation of a chemical reaction which proceeds with a change in pH value represents a simple application for the method of the invention. When the reaction ends or is complete at a specific pH value, then a single color indicator or, respectively, pH indicator can be added to the reaction medium which may be a solution and this color indicator or, respectively, the pH indicator will exhibit a change in color at the specific pH value. Methyl orange, for example, is a colorant which has a red color in the highly acidic range and changes to a yellow color with pH value of about 3 through 4.5. Two photodiodes are adequate to observe this reaction since the maximum sensitivity of the diodes may have a sensitivity in the wavelength regions of the two indicator colors. Thus, it is not necessary that the respective sensitivity region of the diodes be sharply limited or narrow. The color allocation is accomplished by evaluating the pattern consisting of the two measured values. Since the pattern is known, based on prior comparative measurements and can be stored in an evaluation unit, the recognition of the color change can be automated and exactly reproduced.

For more complicated problems, a larger number of photodiodes which absorb energy at different wavelengths are required. These photodiodes may be advantageously integrated in a single electrical component. This allows easy and convenient manipulation of the equipment. One embodiment of the invention utilizes a spectrometer diode such as disclosed by W. Albertshofer, A. Gerhard in the article entitled Flussigkeitsanalyse unter Verwendung einer Spektrometer diode, Proceedings of Sensoren-Technologie und Anwendung, Bad Nauheim, FRG, 1986, NTG-Fachberichte 93, appendix, page 30. The spectrometer diode is constructed with a layer structure of semiconductor material having steadily varying band gaps. Under irridation of the diode from the side having the greatest bang gaps, the photons penetrate so deeply into the semiconductor that they will be absorbed in this semiconductor layer which has the band gap corresponding to their energy. A bias grinding of the backside of the diode makes it possible to apply Schottky contacts to different layers which have different band gaps. The signals generated can thus be associated with different wavelengths of the incident light.

Further developments of this spectrometer diode to obtain higher sensitivity are discussed in German Patent Application Nos. P 37 36 201.1 and P 37 43 131.5 in which various methods for the operation of the spectrometer diode are disclosed in German Patent Application No. P 37 36 203.8.

Depending on the particular structure, a spectrometer diode can detect up to about 15 different absorption ranges. The sensitivity regions of the individual diodes can be shifted with suitable operating methods as, for example, by varying the operating voltage of the diode. As a result, more than one signal can be obtained from each individual diode. This increases the density of the measured values and facilitates the evaluations and makes the result more accurate.

The method of the invention can be used for continuous observation of a chemical reaction if one of the reaction components has a color or can be documented using a color indicator. Every individual diode supplies a signal which is dependent on time or, respectively, concentration which can be evaluated using mathematical relationships on the basis of a curve analysis, for example, by forming derivatives and identification of the curve maximums and minimums. Also, further information are obtained which allow an exact identification of the observed concentrations and gives information about the current stage of the chemical reaction at any time.

The continuous observation of the reaction with the method has a further advantage that disturbing sources are almost completely suppressed. Additional colored substances which do not participate in the reaction or obscuring contaminants that make a visual recognition of a color more difficult which may be potentially present in the medium under observation are eliminated as constant "background noise" when making a time dependent measurement.

An additional application of the method of the invention is the identification of a hue. In other words, the measurement of the compensation of a mixed color composed of known colorants. For example, this problem occurs during identification of pH values with mixed indicators. However, color indicators which are used with the invention are also used in other methods, for example, in the identification of specific substances during the analysis of industrial water or of freely flowing waters.

Other objects, features and advantages of the invention will be readily apparent from the following description of certain preferred embodiments thereof taken in conjunction with the accompanying drawings although variations and modifications may be effected without departing from the spirit and scope of the novel concepts of the disclosure, and in which:

DESCRIPTION OF THE PREFERRED EMBODIMENTS

Figure 1:
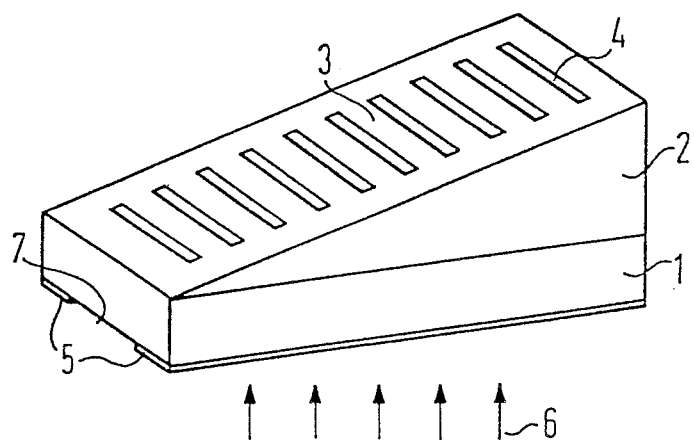
FIG. 1 is a perspective view of a spectrometer diode.

FIG. 1 illustrates a spectrometer diode which is formed from a substrate 1 that might be made of indium phosphide. Upon the substrate 1 is formed a layer structure 2 of generally triangular-shape which might be formed of indium phosphide/arsenide $InP_{1-x}As_x$ which has a steadily varying x, so that x assumes values between 0 and 1. The band gap in the finished crystal of the layer structure 2 decreases steadily as a function of distance from the substrate 1. For example, it is reduced from 1.3 eV in the substrate 1 (InP) to 0.4 eV at the edge of the layer structure 2 (InAs) which is furthest away from the substrate 1.

The surface of the layer 2 facing away from the substrate 1 comprises a slanted plane 3. Schottky contacts 4 are attached to the slanted plane surface 3 and form light sensitive pn junctions which are polarized in the nonconducting direction during operation of the spectrometer diode. Due to the bias grinding, each of the contacts 4 is in communication on the slanted plane 3 with a very specific layer of the layer structure 2 which is beneath it and this particular layer has a specific band gap.

An ohmic contact 5 which is formed with a recess 7 so that incident light 6 can penetrate into the spectrometer diode is formed on the substrate side 1 on the surface which is opposite to the layer structure 2. The light 6 will penetrate as deeply into the layer structure 2 until it can be absorbed in the layer which has a band gap corresponding to the wavelength of the particular light component.

Figure 2:
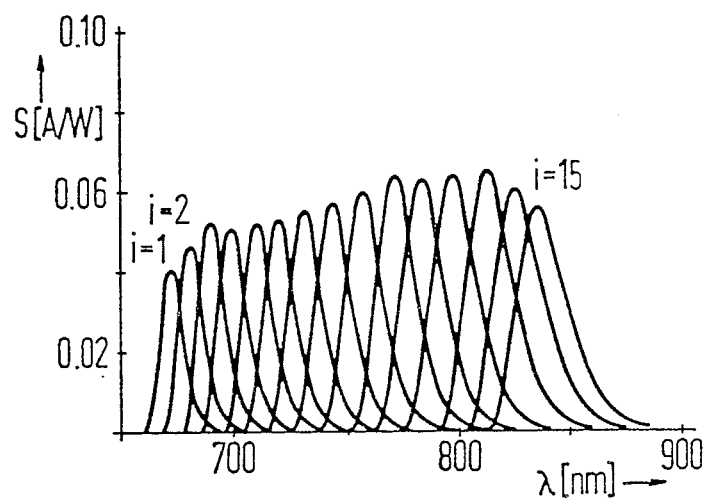
FIG. 2 is a curve showing the absorption regions of individual diodes of the spectrometer device.

FIG. 2 is a plot which shows how each of the contacts 4 act as an independent photodiode with the layer structure lying beneath them. Since the layers lying beneath each of the contacts have a different band gap, each of the "individual diodes" will absorb its own wavelength region. The curves illustrated in FIG. 2 represents the sensitivity of the individual diodes to the light of different wavelengths. The "strength" S of the signal to be output by the respective individual diodes is plotted opposite the wavelengths $\lambda$ of the incident light in FIG. 2. As illustrated in FIG. 2, a sensitivity region of the individual diodes which are continuously numbered by 1 through 15 results which overlap each other. A higher number represents the sensitivity for longer wavelengths and simultaneously corresponds to a diode having a lower band gap. Each individual diode supplies a signal during the measuring event which corresponds to the light absorbed in the sensitivity region of the diode. The individual signals produce a pattern which results in a rastered image of the spectral distribution of the overall light which is received and absorbed by the spectrometer diode.

Figure 3:
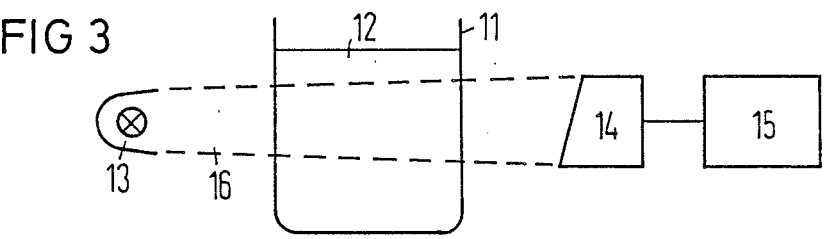
FIG. 3 illustrates an experimental setup for using the method of the invention.

FIG. 3 illustrates apparatus for the implementation of the method of the invention. A light transmissive vessel 11 that may be made of glass for example, is filled with the medium which is to be observed, for example, a solution 12. A light source 13 produces a beam 16 which shines through the vessel 11 and portions of the solution 12 which are located in one side of the vessel 11. The measuring equipment 14 which may be, for example, the previously described spectrometer diode receives the light beam after it has passed through the medium 12 and each of the photodiodes produce electrical outputs which are furnished to the evaluation unit 15 and to which the measuring apparatus 14 is connected. The pH value of the solution 12 can then be identified. For this purpose, a mixed indicator is added to the solution which subsequently assumes a color corresponding to the pH value. The vessel containing the solution 12 is then illuminated with the lamp 13. When the light penetrates the medium 12, specific frequencies from the light are absorbed by the indicator system 14. The light received by the spectrometer diode 14 after it passes through vessel and the solution, will have a spectral distribution which is characteristic of the indicator color. The individual diodes of the spectrometer diode 14 then supply signals which are evaluated in the evaluation unit 15 on the basis of their pattern. The known principal of pattern recognition is based on data which has been identified during a calibration procedure and which are stored in the evaluation unit 15. Such data contains a plurality of individual patterns which can be compared to the current pattern to recognize the specimen under test. The evaluation unit 15 indicates the pH value of the solution 12. It is a prerequisite for the method that the same lamp 13 and the same vessel 12 be used during the calibration procedure and during the measuring procedure. However, the use of a different vessel 11, lamp 13 and spectrometer diode 14 can be used and can be varied between calibration procedure and measuring procedure since the measured pattern is not effected by these parameters. This results in the additional advantage that only an extremely simple optics is required for the measuring method. Thus, the apparatus can be simply and rapidly implemented.

Figure 4:
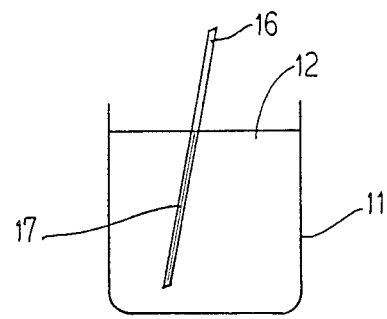
FIG. 4 illustrates a modification of the invention.
Figure 5:
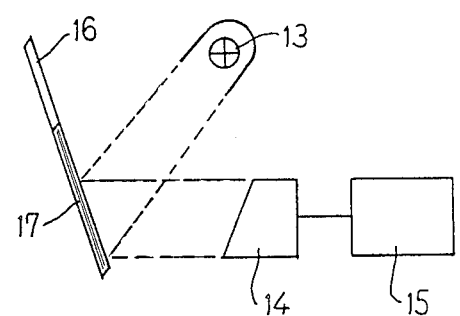
FIG. 5 illustrates the modification of the invention discussed with reference to FIG. 4.

FIGS. 4 and 5 illustrate a second exemplary embodiment wherein for example, color indicators can be applied on solid carriers. For example, this can be an individual indicator, a mixed indicator or a plurality of individual indicators which are applied on the carrier 16 in region 17 which are spatially separated from each other. For example, in a number of test strips as utilized, for example, in water or urine examinations, in water analysis and medical diagnostics. So as to implement the method of the invention, the test strip 17 mounted on a carrier 16 is placed in contact with the medium 12 for a prescribed length of time. The medium 12 in the container 11 contains the substance which is to be observed. The carrier 16 with the strip 17 is dipped into the solution 12 and the indicator reaction of the test strip 17 occurs due to contact with the substance which is to be observed are measured. The regions of the indicator strip 17 will take on a characteristic coloration after being dipped into the solution 12 and the test strip 17 can be removed from solution and then be illuminated with a light 13 so as to produce reflected light which is received by the spectrometer diode 14. The pattern characteristic of the indication coloration and identification of the individual diodes of the spectrometer diode 14 can be made by supplying the output of the spectrometer diode 14 to an evaluation unit 15 which compares the output to value which are stored and which were obtained from a series of calibration measurements. The evaluation unit 15 recognizes patterns which coincide and based on the comparison produces an output which indicates the concentration of the substance which is to be measured.

The invention allows concentration identification to be easily made by recognizing the indicator color so that rapid and exact results can be obtained. The measuring apparatus is simple and can be easily moved about. Thus, the method and apparatus of the invention can be performed outside of a laboratory as, for example, outdoors.

Although the invention has been described with respect to preferred embodiments, it is not to be so limited as changes and modifications can be made which are within the full intended scope of the invention as defined by the appended claims.

I claim as my invention:

1. A method for optical identification of the concentration of at least one substance which can be observed in a medium directly due to an inherent color of the substance or substances or indirectly using a color indicator, comprising the steps of measuring light emitted by the medium (12) which indicates the color with a plurality of independent photodiodes which are sensitive in different absorption regions to form the measured values in a pattern matrix, and evaluating them using pattern recognition, and identifying the concentration of the substance or substances using known comparison values, wherein photodiodes which are integrated on a single electrical component (14) are employed, and wherein a spectrometer diode (14) is employed as the integrated component and which comprises a plurality of electrically independent individual diodes located on a single semiconductor body with layer structure, whereby the optical band spacing of the layers of the semiconductor body steadily varies and the electrical contacts of the individual diodes are applied on different layers of the semiconductor body.

2. A method according to claim 1 wherein the medium that has the color is a solution (12) that is at least partly transirradiated by light from a constant radiation source (13); and the light is measured by the photodiodes received through the solution (12).

3. A method according to claim 1 wherein a color indicator which is applied to a solid carrier is used which is brought into contact with the substance during a fixed time with the medium that contains the substance to be observed, and the color of the color indicator is identified using the photodiodes.

4. A method according to claim 1 wherein continuous observations of a chemical reaction are made.

* * * * *